(12) United States Patent
Wigbers et al.

(10) Patent No.: US 10,414,716 B2
(45) Date of Patent: Sep. 17, 2019

(54) PROCESS FOR PREPARING A POLYETHERAMINE

(71) Applicant: BASF SE, Ludwigshafen (DE)

(72) Inventors: Christof Wilhelm Wigbers, Lich (DE); Wolfgang Mägerlein, Limburgerhof (DE); Thomas Krug, Worms (DE); Johann-Peter Melder, Böhl-Iggelheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 15/534,856

(22) PCT Filed: Dec. 1, 2015

(86) PCT No.: PCT/EP2015/078126
§ 371 (c)(1),
(2) Date: Jun. 9, 2017

(87) PCT Pub. No.: WO2016/091643
PCT Pub. Date: Jun. 16, 2016

(65) Prior Publication Data
US 2017/0362164 A1    Dec. 21, 2017

(30) Foreign Application Priority Data
Dec. 12, 2014 (EP) .................... 14197758

(51) Int. Cl.
| | | |
|---|---|---|
| *B01J 21/04* | (2006.01) |
| *B01J 21/06* | (2006.01) |
| *B01J 23/04* | (2006.01) |
| *B01J 23/14* | (2006.01) |
| *B01J 23/28* | (2006.01) |
| *B01J 23/72* | (2006.01) |
| *B01J 23/75* | (2006.01) |
| *C08G 65/26* | (2006.01) |
| *B01J 23/755* | (2006.01) |
| *C07C 213/02* | (2006.01) |

(52) U.S. Cl.
CPC ............ *C07C 213/02* (2013.01); *B01J 21/04* (2013.01); *B01J 21/066* (2013.01); *B01J 23/04* (2013.01); *B01J 23/14* (2013.01); *B01J 23/28* (2013.01); *B01J 23/72* (2013.01); *B01J 23/75* (2013.01); *B01J 23/755* (2013.01); *C08G 65/2621* (2013.01); *C08G 65/2648* (2013.01); *C08G 65/2696* (2013.01); *Y02P 20/582* (2015.11)

(58) Field of Classification Search
CPC .......... B01J 21/04; B01J 21/066; B01J 23/04; B01J 23/14; B01J 23/28; B01J 23/72; B01J 23/75; B01J 23/755; C07C 213/02; C08G 65/2621; C08G 65/2648; C08G 65/2696
See application file for complete search history.

(56) References Cited

U.S. PATENT DOCUMENTS

| | | | |
|---|---|---|---|
| 3,580,952 A | 5/1971 | Moschel | |
| 4,766,245 A * | 8/1988 | Larkin | ............... C08G 65/3255 564/474 |
| 5,254,227 A * | 10/1993 | Cawlfield | ............ B01D 53/326 204/536 |
| 5,530,127 A | 6/1996 | Reif et al. | |
| 5,536,691 A | 7/1996 | Breitscheidel et al. | |
| 5,696,048 A | 12/1997 | Breitscheidel et al. | |
| 8,487,135 B2 | 7/2013 | Kubanek et al. | |
| 2003/0089592 A1* | 5/2003 | Wolfert | ................ C07D 207/04 203/33 |
| 2003/0144367 A1* | 7/2003 | Jacobus Van Berge | ..................... B01J 23/75 518/715 |
| 2011/0009627 A1 | 1/2011 | Schmidtke et al. | |
| 2011/0137030 A1* | 6/2011 | Kubanek | ................ B01J 23/835 544/178 |

FOREIGN PATENT DOCUMENTS

| | | |
|---|---|---|
| EP | 636409 A1 | 2/1995 |
| EP | 696572 A1 | 2/1996 |
| EP | 742045 A1 | 11/1996 |
| EP | 1028138 A2 | 8/2000 |
| JP | S49014158 B1 | 4/1974 |
| JP | S49014159 B1 | 4/1974 |
| WO | WO-07096317 A1 | 8/2007 |
| WO | WO-20090092724 A1 | 7/2009 |

(Continued)

OTHER PUBLICATIONS

International Preliminary Examination Report with Applicant amendments (in German) for PCT/EP2015/078126 dated Nov. 16, 2016.

(Continued)

*Primary Examiner* — Pancham Bakshi
*Assistant Examiner* — Mark R Luderer
(74) *Attorney, Agent, or Firm* — Drinker Biddle & Reath LLP

(57) ABSTRACT

A process for producing a polyetheramine by reacting a polyether alcohol, previously synthesized in the presence of a basic potassium or sodium compound as catalyst, with ammonia in the presence of hydrogen and a catalyst in one reactor or a plurality of reactors, wherein the employed polyether alcohol when previously synthesized in the presence of a basic potassium compound as catalyst has a content of potassium ions of less than 50 wppm and when previously synthesized in the presence of a basic sodium compound as catalyst has a content of sodium ions of less than 50 wppm.

26 Claims, No Drawings

(56) References Cited

FOREIGN PATENT DOCUMENTS

| WO | WO-2011067199 A1 | 6/2011 |
| WO | WO-2011087793 A1 | 7/2011 |
| WO | WO-2014009292 A1 | 1/2014 |
| WO | WO-2014184039 A1 | 11/2014 |
| WO | WO-2014184048 A1 | 11/2014 |

OTHER PUBLICATIONS

International Search Report for PCT/EP2015/078126 dated Jan. 18, 2016.
Extended European Search Report for EP Patent Application No. 14197758.7, dated May 29, 2015.
"Fixed-Bed Reactors", Ullmann's Encyclopedia of Industrial Chemistry, 1992, vol. B4, 5th ed., pp. 199-238.

* cited by examiner

PROCESS FOR PREPARING A POLYETHERAMINE

CROSS-REFERENCE TO RELATED APPLICATIONS

This application is a national stage application (under 35 U.S.C. § 371) of PCT/EP2015/078126, filed Dec. 1, 2015, which claims benefit of European Application No. 14197758.7, filed Dec. 12, 2014, both of which are incorporated herein by reference in their entirety.

The present invention relates to a process for producing a polyetheramine by reacting a polyether alcohol, previously synthesized in the presence of a basic potassium or sodium compound as catalyst, with ammonia in the presence of hydrogen and a catalyst in one reactor or a plurality of reactors.

The process products are used, inter alia, in polyurethane, polyurea and epoxy applications. They are employed, for example, for curing epoxy resins, for example in the production of rotor blades for wind turbines and in the production of coatings, glues and adhesives. Said products are further used in crude oil extraction and in the construction industry.

WO 2011/067199 A1 (BASF SE) relates to particular aluminum oxide-, copper-, nickel-, cobalt-, and tin-containing catalysts and the use thereof in processes for producing an amine from a primary or secondary alcohol, aldehyde and/or ketone. The production of polyetheramines from corresponding polyether alcohols and ammonia is referred to in general terms on page 26, lines 1 to 5.

EP 696 572 A1 (BASF AG) relates to aminating hydrogenations using $ZrO_2$/CuO/NiO/$MoO_3$ catalysts. This document teaches the production of polyetheramines from corresponding polyether alcohols and aminating agents such as ammonia in general terms and describes said production in Example 9 (page 11).

WO 09/092724 A1 (BASF SE) teaches reactors for carrying out high-pressure reactions and, inter alia, a process for producing polyetheramines from the corresponding polyether alcohols and ammonia carried out in such reactors.

EP 1 028 138 A2 (BASF Corp.) describes the production of polyether alcohols from corresponding alkylene oxides by polymerization in the presence of alkaline catalysts, for example potassium hydroxide, i.e. a potassium compound. The alkaline catalyst in the crude product is neutralized using a carboxylic acid and the removal of the salt formed, e.g. a potassium salt, as a separate step is not disclosed (cf. paragraphs [0002], [0003] and [0004] for example).

WO 07/096317 A1 (BASF AG) discloses that a potassium content in polyether alcohols is disadvantageous for foam applications (cf. paragraphs [0002] and [0003] for example). This document contains no teaching concerning the production of polyetheramines.

U.S. Pat. No. 3,580,952 A (Farbwerke Hoechst AG) relates to a method of polyetheramine production by reaction of polypropylene oxide with ammonia and teaches removing salts from the product only after the amination reaction (cf. the abstract for example).

JP 49 014 158 B and JP 49 014 159 B (both Mitsui Toatsu Chem., Inc.) describe an amination of polyether alcohols to polyetheramines, wherein no removal of KOH from the polyether alcohols is carried out prior to the amination.

WO 2011/087793 A1 (Huntsman Petrochemical LLC) relates to etheramines and the use thereof as intermediates in the production of polymers. The use of alkaline catalysts in the alkoxylation of polyhydric alcohols is cited (page 7, lines 3-6) as is the option of removing these catalysts from the crude product after the alkoxylation reaction, for example by vacuum stripping (page 7, lines 6-9) or by neutralization with acids, for example oxalic acid, or by treatment with magnesium silicate and subsequent filtration (page 7, lines 23-25, =first sentence of [0027]).

The production of polyether alcohols from a mono- or polyhydric alcohol by reaction with one alkylene oxide or a plurality of alkylene oxides, for example by reaction of monopropylene or dipropylene glycol with propylene oxide, often employs basic catalysts. The basic catalysts are particularly alkali metal compounds, very particularly sodium or potassium compounds, for example alkali metal alkoxides generally having from 1 to 4 carbon atoms in the alkoxide radical, for example sodium or potassium methoxide, sodium or potassium ethoxide, sodium or potassium isopropoxide, sodium or potassium tert-butoxide or mixtures thereof. The basic catalysts are furthermore particularly alkali metal or alkaline earth metal hydroxides, for example sodium, potassium, calcium or barium hydroxide.

Greatest preference is given to using potassium hydroxide as basic catalyst.

After the reaction the basic catalyst is generally either removed by addition of adsorbents, for example magnesium silicate, and subsequent filtration, or is initially neutralized using an acid, the salts formed then being removed by filtration optionally with the aid of adsorbents, for example magnesium silicate. Neutralization is effected using organic acids, for example acetic acid, or inorganic acids, for example sulfuric acid or phosphoric acid.

The present invention is concerned with polyether alcohols produced using sodium or potassium compounds, particularly potassium compounds, as basic catalysts. After removal of the sodium or potassium catalyst, for example using one of the abovementioned methods, the polyether alcohols produced generally still contain, to a greater or lesser extent, a residual content of sodium or potassium ions.

It has been observed that in the course of the, for example continuous, reaction of a polyether alcohol with ammonia over a catalyst, for example a fixed-bed catalyst, particularly an aluminum oxide-, zirconium dioxide- or chromium oxide-supported copper catalyst, the activity of the amination catalyst steadily decreases. Hence the production temperature always needs to be increased over time during production to compensate for the catalyst activity loss and to achieve the specified conversion (amine numbers, degree of amination). The temperature increase necessary is often associated with an increase in unwanted side reactions (for example cleavage of the ether chains to form shorter aminated fractions which may react to form unwanted by-products such as, for example, dimethylmorpholine, or increased formation of secondary/tertiary amines). As soon as the maximum possible/useful reaction temperature has been achieved, the catalyst may be washed clean of deposits by rinsing with a suitable solvent, for example water and/or ammonia, if it is to be used further. Following such rinsing, for example water rinsing, the catalyst again achieves a substantially higher activity or even the original activity and the amine number specification of the polyetheramine is once again achieved at relatively low temperatures.

The present invention has for its object to improve the economy of existing processes for producing polyetheramines from polyether alcohols produced in the presence of a basic sodium or potassium compound as catalyst and to remedy one or more disadvantages of the prior art. The intention was to find measures that may be carried out industrially in simple fashion and that allow the process to be carried out with high conversion, high yield, space-time yield, selectivity, while at the same time preferably achieving good mechanical stability of the catalyst, for example of a shaped catalyst body.

It has now been found that the catalyst activity can be maintained for longer by avoiding or at least reducing the presence of sodium ions and potassium ions in the polyether alcohol employed. In the, for example continuous, amination of the polyol sodium and potassium ions act as catalyst poison (presumably via the deposition thereof on the catalyst). It is furthermore possible to remove deposited sodium compounds and potassium compounds from the reactor/the reactors containing the catalyst, for example via a water and/or ammonia rinse, and hence to restore the activity of the catalyst. This is achieved in an all the more rapid (rinsing time) and catalyst-friendly fashion the greater the reduction in the sodium and potassium ion content of the polyether alcohols employed.

We have accordingly found a process for producing a polyetheramine by reacting a polyether alcohol, previously synthesized in the presence of a basic potassium or sodium compound as catalyst, with ammonia in the presence of hydrogen and a catalyst in one reactor or a plurality of reactors, wherein the employed polyether alcohol when previously synthesized in the presence of a basic potassium compound as catalyst has a content of potassium ions of less than 50 wppm and when previously synthesized in the presence of a basic sodium compound as catalyst has a content of sodium ions of less than 50 wppm.

Particular preference is given to the process for producing a polyetheramine by reacting a polyether alcohol, previously synthesized in the presence of a basic potassium compound as catalyst, with ammonia in the presence of hydrogen and a catalyst in one reactor or a plurality of reactors, wherein the employed polyether alcohol previously synthesized in the presence of a basic potassium compound as catalyst has a content of potassium ions of less than 50 wppm.

Avoiding frequent catalyst rinsing cycles/increasing the duration of the production periods between two rinses achieves an increase in capacity. In addition, the longer-lasting high catalyst activity allows production at lower temperatures which increases selectivity (i.e. side-reactions are avoided) and keeps the reaction temperature further below maximum safe operating temperatures (reaction runaway may be possible at excessive temperatures). The process according to the invention alternatively makes it possible to run a higher catalyst space velocity (kg Polyetheralkohol/($l_{cat.}$·h)) at a given temperature.

The basic sodium compound is, for example, sodium hydroxide or a sodium alkoxide, for example sodium methoxide, ethoxide, isopropoxide, or tert-butoxide, in particular sodium hydroxide.

The basic potassium compound is, for example, potassium hydroxide or a potassium alkoxide, for example potassium methoxide, ethoxide, isopropoxide, or tert-butoxide, in particular potassium hydroxide.

The polyether alcohol employed in particular has a content of potassium/sodium ions of less than 25 wppm, more particularly of ≤20 wppm, preferably in the range of from 0 to <20 wppm, for example in the range of from 1 to 18 wppm, more preferably of ≤15 wppm, more preferably of <10 wppm, most preferably of <8 wppm, for example in the range of from 2 to 7 wppm (in each case based on 100% pure polyether alcohol).

Such a content of potassium/sodium ions in the polyether alcohol may be achieved via measures known to those skilled in the art, for example from EP 1 028 138 A2 (BASF Corp.), in particular paragraph [0002] therein, or from WO 2011/087793 A1 (Huntsman Petrochemical LLC), in particular page 7, lines 6-9 and 23-25 therein.

Preferred methods of establishing a content of potassium and sodium ions of less than 25 wppm, more particularly of ≤20 wppm, preferably in the range of from 0 to <20 wppm, for example in the range of from 2 to 18 wppm are:

- vacuum stripping of the polyether alcohol to remove the polyether alcohol, from the basic potassium/sodium compound, overhead.
- treatment with a magnesium silicate, for example Ambosol® in the presence of a small amount of water (for example 1 wt % of $H_2O$ based on the pure polyether alcohol) and subsequent filtration to leave the formed potassium/sodium salts behind in the filter cake: See http://www.pqcorp.com/pc/EMEA/Markets/Polyol-Purification for example.
- treatment with a commonly used ion exchanger for cations.
- neutralization of the basic potassium/sodium compound with an acid, particularly an inorganic acid, in particular phosphoric acid, to precipitate the potassium or sodium in the form of sparingly soluble salts and subsequent filtration to leave the relevant potassium/sodium salts behind in the filter cake.
- neutralization of the basic potassium/sodium compound with an acid, for example acetic acid, to form readily soluble/partially soluble potassium/sodium salts and treatment with a magnesium silicate, for example Ambosol®, and subsequent filtration to leave the relevant potassium/sodium salts behind in the filter cake.

The process according to the invention for producing a polyetheramine is preferably carried out over a heterogeneous catalyst.

When the catalyst is arranged as a fixed bed it may be advantageous for the selectivity of the reaction to mix the catalyst, for example the shaped catalyst bodies, in the reactor/in the reactors with inert packing elements, i.e. to "dilute" said catalyst bodies as it were. The proportion of the packings in such catalyst preparations may be from 20 to 80, particularly from 30 to 60, and especially from 40 to 50 parts by volume.

The heterogeneous catalyst may be in the form either of a suspension or of a fixed bed.

In the case of a suspension-catalyzed amination the process may be carried out, for example, in one or more stirred reactor(s), in one or more bubble-column reactor(s) or in one or more jet loop reactor(s).

The amination of the polyether alcohols is preferably carried out in fixed-bed reactors, more preferably in shaft reactors and tube bundle reactors.

Examples of suitable reactors comprising a cycle gas stream may be found in Ullmann's Encyclopedia of Industrial Chemistry, 5th edn., vol. B 4, pages 199-238, "Fixed-Bed Reactors".

In each case the reactors may be employed as a single reactor, as a series of individual reactors and/or in the form of two or more parallel reactors.

When reactors are connected in series, an intermediate introduction of feed (comprising the polyether alcohol and/or ammonia and/or $H_2$) and/or cycle gas and/or fresh gas and/or reactor output from a downstream reactor may optionally be provided.

When reactors are connected in series, one or more heat exchangers may optionally be connected between the reactors to establish the desired temperature.

The specific reactor setup and the performance of the reaction may be varied depending on the specific polyether alcohol to be reacted, the reaction times necessary and the composition of the catalyst employed.

The flow direction of the reactants (polyether alcohol, ammonia, optionally hydrogen, optionally recycled gases and/or liquids) in fixed bed reactors is generally from top to bottom (downflow mode) or from bottom to top (upflow mode).

The reaction may be carried out continuously or batchwise. Continuous mode is preferred. For continuous mode the catalyst is preferably arranged in the reactor/in the reactors as a fixed bed.

The process may be carried out in isothermal or adiabatic fashion. An isothermal operating mode may be achieved, for example, by removing the reaction enthalpy liberated during the amination of the polyether alcohols in the reactor/in the reactors via suitable internal or external cooling devices. In the context of the present invention essentially isothermal conditions is to be understood as meaning that the temperature inside the tube increases by no more than 6 K, preferably by no more than 3 K. The temperature difference is determined from the temperature at the reactor outlet and the temperature at the reactor inlet.

An isothermal mode may particularly preferably be effected in one or more tube bundle reactors.

Tube bundle reactors of the type described in WO 09/092724 A1 (BASF SE) may be employed. It is preferable when the catalyst and the reaction medium are disposed inside the tubes and the cooling medium is disposed in the shell space around the tubes. In one particularly preferred embodiment boiling water is used as cooling medium.

Depending on the operating conditions of the tube bundle reactor(s) it is possible to go from a purely isothermal operating mode (with the abovementioned temperature increase over the catalyst bed) toward an adiabatic operating mode where the temperature increase in the tubes may then be up to 15 K in the case of polyetheramine D230 (see below) for example.

For an adiabatic operating mode the reaction enthalpy liberated is not removed but rather remains in the reaction mixture. When the reaction is carried out in one or more fixed bed reactor(s) an adiabatic process mode results in the reaction mixture increasing in temperature by up to 30° C. or more during passage through the reactor depending on the reaction conditions employed, for example ammonia/polyether alcohol molar ratio (see below), pressure and optionally cycle gas amount. To control and monitor the temperature the reactor/the reactors may have a plurality of measuring points installed therein.

The adiabatic temperature increase may also be limited by recycling a fraction of the liquid crude output from the amination back to the reactor inlet and passing said fraction through the reactor together with the polyether alcohol and the ammonia.

The catalyst space velocity in continuous mode is in particular in the range of from 0.01 to 10, preferably in the range of from 0.1 to 2.0, more preferably in the range of from 0.15 to 1.0, kg of polyether alcohol per liter of catalyst (bed volume) per hour.

The reactants may optionally be diluted with a suitable nonpolar or preferably polar solvent, such as tetrahydrofuran, dioxane or ethylene glycol dimethyl ether.

The process according to the invention for amination of polyether alcohols is preferably carried out at a temperature in the range of from 150° C. to 240° C., in particular in the range of from 170° C. to 230° C., more particularly in the range of from 180° C. to 220° C., very particularly in the range of from 190° C. to 215° C.

The reaction is preferably performed in the liquid phase. The reactant alcohol and the product amine are thus present in the reactor/in the reactors in liquid form under the reaction conditions.

The reaction pressure is preferably from 50 to 220 bar, more preferably from 75 to 200 bar, in particular from 100 to 180 bar, more particularly from 110 to 160 bar.

The pressure in the reaction vessel, which is the sum of the partial pressures of ammonia, of the polyether alcohol, of the reaction products formed and of any solvent and/or recycled gaseous or liquid components at the indicated temperatures, is advantageously increased to the desired reaction pressure by introduction of the hydrogen.

Ammonia is preferably used in a molar ratio in the range of from 1.5 to 500 per mole of alcoholic hydroxyl group in the polyether alcohol. This molar ratio is in particular in the range of from 3 to 150, more particularly in the range of from 5 to 120.

The value chosen in respect of this molar ratio may depend on the type of the polyether alcohol employed.

Thus, for example, for the amination of polypropylene glycol P230 (a mixture of molecules of formula IIa having an average molar mass in the range of from 210 to 250 g/mol, in particular of 230 g/mol) this molar ratio is preferably in the range of from 5 to 20. For the amination polypropylene glycol P2000 (a mixture of molecules of formula IIb having an average molar mass in the range of from 1900 to 2100 g/mol, in particular of 2000 g/mol) this molar ratio is preferably in the range of from 75 to 120.

The amination of the polyether alcohols is carried out in the presence of hydrogen.

After passage through the reactor/the reactors the hot reaction mixture is generally cooled down using a heat exchanger or else a plurality of heat exchangers. The heat exchangers may, for example, be operated with air or with water as cooling medium. The cold feed mixture to the reactor may also serve as cooling medium.

In order to separate gaseous components from liquid components the reaction mixture is advantageously passed into one or more separation vessels which are generally operated at different pressures. The gaseous components may either be passed back to the reactor inlet as cycle gas or discharged from the process as offgas.

A distinction may be made between a mode where the gas phase is passed through the reactor(s) in straight pass and after passage through the reactor(s) is discharged as offgas (=fresh gas mode) and a mode where after passage through the reactor(s) the gas phase is completely or partially recycled to upstream of the reactor (=cycle gas mode). For the cycle gas mode it is industrially possible to use a cycle gas compressor which, after the gas phase has passed through the reactor and the liquid phase has been removed, recompresses said gas phase and recycles it to the reactor inlet.

For a fresh gas mode it is preferable to pass hydrogen into the reactor in an amount of from 1 to 200 $Nm^3/[m^3$ of catalyst (bed volume)·h], preferably from 5 to 100 $Nm^3/[m^3$ of catalyst (bed volume)·h]. Since this hydrogen amount is lost as offgas, the amount selected is, inter alia, a commercial consideration.

For a cycle gas mode the cycle gas amount is preferably in the range of from 50 to 1000 $Nm^3/[m^3$ of catalyst (bed volume)·h], in particular in the range of from 60 to 300 $Nm^3/[m^3$ of catalyst (bed volume)·h].

The cycle gas preferably comprises at least 10, in particular from 50 to 100 and very particularly from 60 to 95 vol % of $H_2$. The remainder is predominantly ammonia. The composition of the cycle gas is also determined by the chosen temperature in the abovementioned separation vessel which may be, for example, in the range of from 0° C. to 60° C., preferably between 20° C. and 40° C.

[Normal cubic meter=$Nm^3$=volume converted to standard conditions (20° C., 1 bar abs.)]. Reported catalyst volumes always relate to the bed volume.

The amination of the polyether alcohols typically achieves degrees of amination in the range of from 60% to 100%, preferably in the range of from 80% to 95%.

It is advantageous to heat the reactants, preferably to the reaction temperature, even before they are supplied to the reaction vessel.

Accordingly a possible continuously operated process concept provides for passing the starting materials (polyether alcohol, ammonia and hydrogen), together with any recycled gas and/or liquid streams, separately or together through one or more preheaters to establish the desired reactor entry temperature. These preheater(s) are typically heated with steam. However, hot reaction output may also be used as heating medium.

The starting materials and any recycled gas and/or liquid streams may be mixed before being passed into the reactor or they may be supplied to the reactor inlet separately.

The liquid reaction output is generally freed of residual catalyst, for example by filtration, cyclones etc.

The liquid reaction output is advantageously worked up in a distillation part.

The liquid reaction output typically still contains excess ammonia. The ammonia is in particular removed by distillation and preferably recycled into the reaction.

The water of reaction formed in the course of the reaction (in each case one mole per mole of alcohol group reacted) is not generally detrimental to the degree of conversion, the reaction rate, the selectivity, or the catalyst lifetime, and is thus advantageously removed from the reaction product only in the distillative workup thereof.

The reaction product is preferably worked up as follows:

Since the polyetheramines are typically high-boiling products, they are preferably obtained as bottom products in the distillation part of the process. Water (see above) and other low-boilers are distilled off overhead.

High bottoms temperatures may be avoided by carrying out the distillative removal of the water and of any other low-boilers under reduced pressure (vacuum).

When the polyetheramine (PEA) is obtained as bottom product, excessively lengthy exposure of the PEA to high temperatures may be avoided by limiting the residence time via the size of the bottom region of the distillation column and/or the throughput.

Such a residence time is preferably in the range of from 5 to 60 minutes.

Preference is given to a procedure where from the reaction product of the reaction, by distillation,
(i) initially any unconverted ammonia is removed overhead and preferably recycled into the process,
(ii) water is removed overhead,
(iii) any by-products present and having a lower boiling point than the process product are removed overhead together with any remaining water,
and (iv) the process product polyetheramine is removed as bottom product.

Preferably producible by the process according to the invention are polyetheramines of the following formula

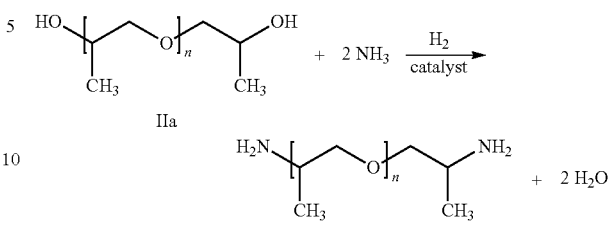

wherein the polyether alcohol IIa (reactant) and the polyetheramine (product) are in each case in the form of a mixture of molecules where n is on average in the range of from 2.3 to 3.0, in particular in the range of from 2.5 to 2.8, and the molar mass of the polyetheramine is on average in the range of from 210 to 250 g/mol, in particular in the range of from 220 to 240 g/mol, for example 230 g/mol.

Also preferably producible by the process according to the invention are polyetheramines of the following formula

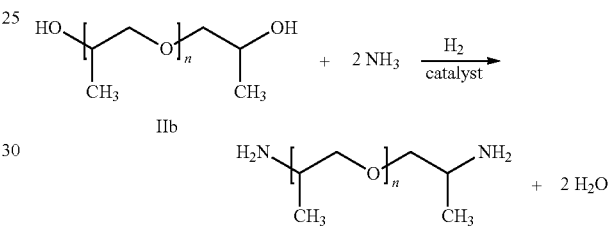

wherein the polyether alcohol IIb (reactant) and the polyetheramine (product) are in each case in the form of a mixture of molecules where n is on average in the range of from 31.5 to 35.0, in particular in the range of from 32.3 to 34.0, and the molar mass of the polyetheramine is on average in the range of from 1900 to 2100 g/mol, in particular in the range of from 1950 to 2050 g/mol, for example 2000 g/mol.

The catalyst preferably employed in the process according to the invention comprises copper and/or cobalt and/or nickel.

It is preferable when prior to its reduction with hydrogen the catalytically active mass of the catalyst comprises oxygen-containing compounds of aluminum and/or zirconium and/or chromium and oxygen-containing compounds of copper.

It is further preferable when prior to its reduction with hydrogen the catalytically active mass of the catalyst comprises oxygen-containing compounds of aluminum and/or zirconium and/or chromium and oxygen-containing compounds of copper and nickel.

It is further preferable when prior to its reduction with hydrogen the catalytically active mass of the catalyst comprises oxygen-containing compounds of aluminum and/or zirconium and oxygen-containing compounds of copper and cobalt and nickel.

In one particular embodiment, prior to its reduction with hydrogen, the catalytically active mass of the catalyst comprises oxygen-containing compounds of aluminum, copper, nickel and cobalt and from 0.2 to 5.0 wt %, preferably from 0.4 to 4 wt %, of oxygen-containing compounds of tin, calculated as SnO.

By way of example, the catalyst disclosed in WO 2011/067199 A1 (BASF SE) and, for example, also in WO 2014/009292 A1 or in PCT/EP2014/059181, in which prior to its reduction with hydrogen the catalytically active mass of the catalyst comprises in the range of from 15 to 80 wt %, in particular from 30 to 70 wt %, more particularly from 35 to 65 wt %, of oxygen-containing compounds of aluminum, calculated as $Al_2O_3$, from 1 to 20 wt %, in particular from 2 to 18 wt %, more particularly from 5 to 15 wt %, of oxygen-containing compounds of copper, calculated as CuO, from 5 to 35 wt %, in particular from 10 to 30 wt %, more particularly from 12 to 28 wt %, very particularly from 15 to 25 wt %, of oxygen-containing compounds of nickel, calculated as NiO, from 5 to 35 wt %, in particular from 10 to 30 wt %, more particularly from 12 to 28 wt %, very particularly from 15 to 25 wt %, of oxygen-containing compounds of cobalt, calculated as CoO, and from 0.2 to 5.0 wt %, in particular from 0.4 to 4.0 wt %, more particularly from 0.6 to 3.0 wt %, more particularly from 0.7 to 2.5 wt %, of oxygen-containing compounds of tin, calculated as SnO, is advantageously employable.

In this catalyst the molar ratio of nickel to copper is preferably greater than 1, more preferably greater than 1.2, yet more preferably in the range of from 1.8 to 8.5.

The BET surface area (ISO 9277:1995) of this catalyst is preferably in the range of from 30 to 250 $m^2/g$, in particular in the range of from 90 to 200 $m^2/g$, more particularly in the range of from 130 to 190 $m^2/g$ (in each case prior to the reduction with hydrogen). These ranges are attained in particular by calcining temperatures during catalyst production in the range of from 400° C. to 600° C., particularly from 420° C. to 550° C.

In particular, for example, the catalyst disclosed in WO 2011/067199 A1, Example 5, pages 28 and 29, may be employed.

By way of example, in another particular embodiment, the catalyst disclosed in EP 696 572 A1 (BASF SE) and, for example, also in PCT/EP2014/059145, in which prior to its reduction with hydrogen the catalytically active mass of the catalyst comprises in the range of from 20 to 85 wt %, preferably from 20 to 65 wt %, more preferably from 22 to 40 wt %, of oxygen-containing compounds of zirconium, calculated as $ZrO_2$, from 1 to 30 wt %, particularly preferably from 2 to 25 wt %, of oxygen-containing compounds of copper, calculated as CuO, from 14 to 70 wt %, preferably from 15 to 50 wt %, more preferably from 21 to 45 wt %, of oxygen-containing compounds of nickel, calculated as NiO, it being preferable when the molar ratio of nickel to copper is greater than 1, in particular greater than 1.2, very particularly from 1.8 to 8.5, and from 0 to 5 wt %, in particular from 0.1 to 3 wt %, of oxygen-containing compounds of molybdenum, calculated as $MoO_3$, is also advantageously employable.

In particular, for example, the catalyst disclosed in EP 696 572 A1, page 8, having the composition 31.5 wt % $ZrO_2$, 50 wt % NiO, 17 wt % CuO and 1.5 wt % $MoO_3$.

The reported concentrations (in wt %) of the components of the catalyst in each case relate to the catalytically active mass of the produced catalyst following the last of any heat treatments and prior to its reduction with hydrogen.

The catalytically active mass of the catalyst, after the last of any heat treatments and prior to its reduction with hydrogen, is defined as the sum of the masses of the catalytically active constituents and of the catalyst support materials (aluminum oxide/zirconium oxide) and comprises essentially the following constituents:

aluminum oxide ($Al_2O_3$)/zirconium dioxide ($ZrO_2$), oxygen-containing compounds of copper and nickel and optionally of molybdenum or cobalt and tin.

The sum of the abovementioned constituents of the catalytically active composition is typically from 70 to 100 wt %, preferably from 80 to 100 wt %, more preferably from 90 to 100 wt %, in particular >95 wt %, very particularly >98 wt %, especially >99 wt %, for example particularly preferably 100 wt %.

In a further particular embodiment preference is given to catalysts having a content of cobalt and/or nickel of more than 90 wt %, in particular of more than 95 wt %, in each case based on the total catalyst weight excluding any support material.

Preference is also given to catalysts having a content of aluminum+cobalt and/or nickel of more than 80 wt %, in particular of more than 90 wt %, in each case based on the total catalyst weight excluding any support material.

Such preferred catalysts include cobalt sponge catalysts and nickel sponge catalysts which may be produced, for example, from Co/Al or Ni/Al alloys.

Examples of suitable catalysts include Raney® cobalt and Raney® nickel and these catalysts, which comprise aluminum, may also be doped with further metals, such as Cr and/or Mo and/or Fe and/or other metals of group VIII of the periodic table (Chemical Abstracts Service group notation).

In a further particular embodiment preference is given to cobalt-containing catalysts comprising manganese and phosphorus, preference in particular being given to the catalysts taught in EP 636 409 A1 and EP 742 045 A1 (both BASF AG) which have a catalytically active mass consisting of from 55 to 98 wt % cobalt, from 0.2 to 15 wt % phosphorus, from 0.2 to 15 wt % manganese and from 0.05 to 5 wt % alkali metal, in each case calculated as oxide, wherein in particular the calcined catalysts are reduced in a hydrogen stream at end temperatures of from 200° C. to 400° C. and subsequently incipiently surface-oxidized by treatment in a stream of air at end temperatures of from 20° C. to 60° C.

The cobalt catalysts have a specific surface area (ISO 9277:1995) of a 12 $m^2/g$, in particular from 12 to 500 $m^2/g$, preferably from 15 to 200 $m^2/g$, more preferably from 18 to 100 $m^2/g$, and a porosity of a 0.16 $cm^3/g$, in particular from 0.16 to 1.00 $cm^3/g$, preferably from 0.18 to 0.80 $cm^3/g$, more preferably from 0.20 to 0.40 $cm^3/g$ (DIN 66133:1993-06). The catalysts have the additional feature that in the activated state at least 85 wt %, i.e. from 85 to 100 wt %, preferably at least 95 wt %, i.e. from 95 to 100 wt %, of the metallic cobalt is in the hexagonal modification. The catalytically active mass of these cobalt catalysts consists of from 55 to 98 wt %, preferably from 75 to 95 wt %, more preferably from 85 to 95 wt %, cobalt, from 0.2 to 15 wt %, preferably from 0.5 to 10 wt %, more preferably from 1 to 6 wt %, phosphorous, from 0.2 to 15 wt %, preferably from 2 to 10 wt %, more preferably from 3 to 8 wt %, manganese and from 0.05 to 5 wt %, preferably from 0.1 to 3 wt %, more preferably from 0.13 to 1 wt %, alkali metal, in each case calculated as oxide (CoO, $H_3PO_4$, $MnO_2$, alkali metal$_2$O).

Suitable alkali metals are preferably lithium, sodium, potassium and/or cesium, more preferably sodium and/or potassium.

Particular preference is given to catalyst "A" disclosed at the top of page 4 of EP 742 045 A1.

Polyether alcohols that may be employed are monools, diols and/or triols.

Polyether monoalcohols converted into the corresponding polyether monoamines by amination in accordance with the invention are preferably those of general formula I $$R^1-X-OH \qquad (I),$$

where X represents the units

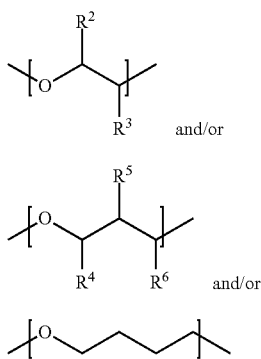

The three units E1, E2 and E3 may each be present in the polyether monoalcohol in a quantity of from 0 to 50, but with the proviso that the quantity of the units sums to at least 2, preferably at least 3, and are arranged in any desired order.

$R^1$ is $C_1$-$C_{30}$ alkyl which may be linear or branched. The radicals $R^2$, $R^3$, $R^4$, $R^5$ and $R^6$ are identical or different and are each independently of one another H or linear $C_1$-$C_{10}$ alkyl.

The units E1 and/or E2 comprised in the polyether monoalcohol may each have identical or different substitutions.

It is preferable to employ polyether monoalcohols comprising only units E1, where $R^2$ is preferably hydrogen and $R^3$ is hydrogen or linear $C_1$-$C_{10}$ alkyl.

Preferred polyether monoalcohols have a molecular weight in the range of from a 100 g/mol, in particular from 200 to 5000 g/mol.

When polyether diols are used to produce the polyetheramines preference is given to using polyether dials based on propylene oxide and/or ethylene oxide and/or butylene oxide and/or pentylene oxide. However it is also possible for the ether oxygens of the polyether diols used to produce the polyetheramines to be bridged by an alkylene group composed of three or more carbon atoms. Examples of suitable diols that may be employed for synthesizing polyetheramines include those of general formulae II, III and IV.

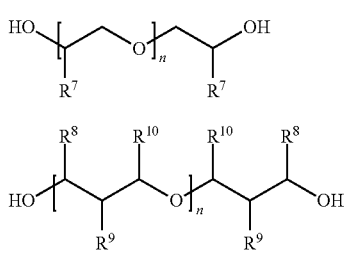

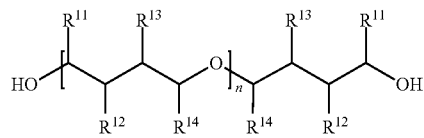

In each case n represents an integer between 1 and 50, $R^7$ represents hydrogen or linear $C_1$-$C_{10}$ alkyl, and $R^8$ to $R^{14}$ are identical or different and independently of one another represent hydrogen or methyl. It should be noted that, for example in general formula II, units E4

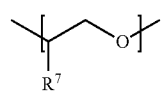

having identical or different radicals $R^7$ appear and in the latter case units having different substitutions are present in the particular polyether diol in any desired sequence and repetition. The same applies analogously to the polyether diols comprising the units E5/E6

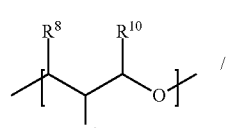

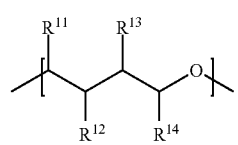

for the radicals $R^8$ to $R^{14}$.

Preferred polyether diols have a molecular weight in the range of from 200 to 5000 g/mol.

It is furthermore possible to employ polyether triols for the synthesis of polyetheramines. The polyether triols are preferably those of general formula V.

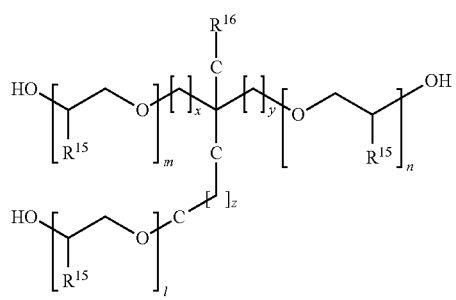

Here, m, n, and l are identical or different and each independently represent an integer between 1 and 50, x, y, and z are identical or different and each independently represent 0 or 1, where, generally, at most one of the three coefficients x, y and z is 0. $R^{15}$ is hydrogen or linear $C_1$-$C_{10}$ alkyl and $R^{16}$ is hydrogen or linear or branched $C_1$-$C_{10}$ alkyl. When repeat units comprising different radicals $R^{15}$ occur within formula V said repeat units may have any desired sequence and repetition.

Preferred polyether triols have a molecular weight in the range of from 250 g/mol, in particular from 400 to 5000 g/mol.

It is preferable when the polyether alcohol to be reacted in accordance with the invention is a secondary alcohol and the polyetheramine thus obtained is a primary amine.

All reported pressures relate to absolute pressure.
All reported ppm values relate to mass.

EXAMPLES

1. Production of Catalyst A

Catalyst A was produced according to Example 5 of WO 2011/067199 A1 (BASF SE). The catalyst thus obtained had the composition shown in table I below.

TABLE I

| Catalyst*) | Ni % | Co % | Cu % | Sn % | BET**) $m^2$/g | Support |
|---|---|---|---|---|---|---|
| Catalyst A | 18.6 | 17.3 | 10.6 | 1.1 | 187 | $Al_2O_3$ |

*)Catalyst composition in wt %; remainder up to 100 wt % is the support
**)ISO 9277: 1995

2. Reaction of Polyether Alcohol (Pluriol®) P230 with Ammonia to Afford PEA D230 in a Continuously Operated Tubular Reactor A reproducible correlation between the potassium ion concentration in the polyether alcohol and the speed of catalyst deactivation was determined by simultaneously carrying out two tests using the same batch of the alcohol amination catalyst A (in the form of 1.0-1.6 mm spall produced from the reduced and passivated tablets), wherein Pluriol® P230 feeds having potassium ion contents of 5 ppm and 10-15 ppm were compared.

Example 2a (P230 Comprising 5 Ppm of $K^+$)

A heated tubular reactor having an internal diameter of 14 mm, a centrally mounted thermocouple and a total volume of 89 ml was charged in the lower part with a layer of glass spheres (15 ml) and on top of that with 70 ml of the reduced amination catalyst A, and finally the remaining part was in turn charged with glass spheres. Prior to the reaction, the catalyst was activated at not more than 280° C. under hydrogen (25 Nl/h) [Nl=normal liter=volume converted to standard conditions (20° C., 1 bar abs.)] at atmospheric pressure for 12 hours. Passed through the reactor from bottom to top were 17.5 g/h of Pluriol® P230 comprising 5 ppm of $K^+$, 28 g/h of liquid ammonia and 8 Nl/h of hydrogen. The reactor was maintained at a temperature of 193° C. and a total pressure of 120 bar. Following sampling after 1145 hours the temperature was increased to 203° C. Following sampling after 1649 hours the plant was rinsed for 5 hours with 30 g/h of water, rinsed for five days with 30 g/h of ammonia and then started up again under the same conditions as before the rinsing.

The mixture exiting the reactor was in each case cooled down and decompressed to atmospheric pressure. Samples of the reaction mixture were taken and analyzed at various time points. The potassium ion content in the feed and in the output was determined regularly prior to the wet-chemistry analysis.

Example 2b (P230 Comprising 10-15 Ppm of $K^+$)

The reaction was carried out analogously to Example 2a in an identically constructed parallel apparatus except that Pluriol® P230 comprising 10-15 ppm $K^+$ was used. Following the water/ammonia rinsing after a run time of 1649 h, the plant was started up under the same conditions as before the rinsing except that Pluriol® P230 having a potassium ion content of 5 ppm was employed. The same catalyst batch was employed and reaction conditions identical to those in Example 2a were run.

TABLE II

| Run time h | Example | AN [mg KOH/g] | AC [mg KOH/g] | tert. AN [mg KOH/g] | Degree of amination [%] | $K^+$ in feed/effluent [ppm] |
|---|---|---|---|---|---|---|
| 41 | 2a | 464.8 | 497.5 | 0.60 | 93.43 | 5/0 |
| | 2b | 464.3 | 500.7 | 0.5 | 92.73 | 10/0 |
| 137 | 2a | 460.0 | 497.5 | 0.94 | 92.47 | 5/0 |
| | 2b | 462.4 | 500.7 | 0.5 | 92.35 | 10/0 |
| 305 | 2a | 442.5 | 501.4 | 0.7 | 88.25 | 5/0 |
| | 2b | 436.6 | 504.3 | 0.4 | 86.58 | 14/0 |
| 473 | 2a | 432.8 | 503.1 | 0.5 | 86.03 | 5/0 |
| | 2b | 417.0 | 505.8 | 0.7 | 82.43 | 15/0 |
| 641 | 2a | 414.3 | 498.4 | 0.4 | 83.13 | 5/0 |
| | 2b | 395.6 | 498.9 | 0.4 | 79.29 | 15/0 |
| 809 | 2a | 396.3 | 504.0 | 0.8 | 78.63 | 5/0 |
| | 2b | 366.8 | 507.0 | 0.8 | 72.35 | 15/0 |
| 977 | 2a | 374.1 | 504.5 | 0.8 | 74.15 | 5/0 |
| | 2b | 335.6 | 504.9 | 0.8 | 66.47 | 15/0 |
| 1145 | 2a | 342.2 | 502.6 | 0.9 | 68.09 | 5/0 |
| | 2b | 304.0 | 503.9 | 0.6 | 60.33 | 15/0 |
| 1169 | 2a | 414.0 | 502.6 | 0.9 | 82.37 | 5/0 |
| | 2b | 388.0 | 503.9 | 0.9 | 77.00 | 15/0 |
| 1337 | 2a | 409.3 | 500.2 | 0.8 | 81.83 | 5/0 |
| | 2b | 387.1 | 498.5 | 1.0 | 77.65 | 15/0 |
| 1505 | 2a | 401.1 | 500.0 | 0.9 | 80.22 | 5/0 |
| | 2b | 371.0 | 497.9 | 0.8 | 74.51 | 15/0 |
| 1649 | 2a | 398.5 | 500.0 | 0.9 | 79.70 | 5/0 |
| | 2b | 362.0 | 494.3 | 0.7 | 73.23 | 15/0 |
| 1697 | 2a | 453.6 | 500.0 | 0.9 | 90.72 | 5/0 |
| | 2b | 388.4 | 500.0 | 0.4 | 77.68 | 5/0 |
| 1745 | 2a | 449.6 | 496.9 | 0.9 | 90.48 | 5/0 |
| | 2b | 386.7 | 502.4 | 0.4 | 76.97 | 5/0 |

Analyses:

Amine Number (AN) Determination:

A weighed sample of the polyetheramine is diluted with methanol and titrated with 1 N HCl.

The amine number (AN) is determined according to the formula (consumption of 1N HCl [ml]·56.1 [mg/ml])/
weighed portion [g]=amine number [mg KOH/g]

Acetylation Number (AC) Determination:

A weighed sample of the polyetheramine is admixed with a weighed excess of acetylation mixture (pyridine, acetic anhydride, glacial acetic acid) and stirred for two hours at 110° C. The mixture is then admixed with water and stirred for a further 10 min. Once cooled down the mixture is titrated with 0.5 N aqueous sodium hydroxide solution. A blank test (acetylation mixture only, no PEA sample) is produced in analogous fashion.

The AC is determined according to the formula (consumption of 0.5 N NaOH [ml] for blank−consumption of 0.5 N NaOH [ml] for sample·56.1 [mg/ml])·0.5/weighed portion [g]=acetylation number [mg KOH/g]

Tertiary Amine Number Determination (Tert. AN):

A weighed sample of the polyether amine is treated with an excess of acetic anhydride to mask the primary and secondary amine functions. The mixture is subsequently titrated with 0.1 N perchloric acid.

The tert. AN is determined according to the formula (consumption of 0.1 N perchloric acid [ml]·5.61 [mg/ml])/weighed portion [g]=tertiary amine number [mg KOH/g]

The degree of amination is the quotient of AN and AC and is reported in percent.

The potassium ion content in the polyether alcohol and in the polyetheramine was determined using inductively coupled plasma atomic emission spectrometry. A Varian 720 ES instrument was used. The sample was pretreated with acid prior to analysis.

Results:

Under identical reaction conditions and subject to experimental error, at the start of the test identical amine numbers were initially obtained over the catalyst A of the same catalyst batch in the two simultaneously operated tubular reactors. The only difference between the two tests was the concentration of potassium ions in the polyether alcohol feed (Example 2a: 5 ppm, Example 2b: 10-15 ppm). The activity of the catalysts in the two reactors was identical at the start of the test. Over the further course of the test, the activity of both catalysts decreased (lower amine number and lower degree of amination), but the activity of the catalyst from Example 2b, which had the higher concentration of potassium ions in its feed, fell more severely. No potassium ions were detectable in the output of either reactor, i.e. the potassium ions remained on the amination catalyst. As the only difference between the two tests, the deposition of potassium ions on the catalyst was evidently responsible for the activity losses. A temperature increase of 10° C. to 203° C. after a test duration of 1169 h enhanced the degree of amination/the amine number in both tests but the activity of the two catalysts having different degrees of potassium ion contamination was different also at this higher temperature (203° C.).

Rinsing of the catalyst with, for example, water/ammonia after a run time of 1649 h almost fully restored the catalyst activity in test 2a, where Pluriol® P230 having a potassium ion content of 5 ppm had been employed, (amine number and degree of amination almost achieve the initial test values) while in test 2b, where Pluriol® P230 having a potassium ion content of 10-15 ppm had been employed, the catalyst activity did not achieve the original condition (amine number and degree of amination fell far short of the initial test values) because the rinsing duration was not yet long enough.

3. Production of Pluriol® P230 Having a Potassium Ion Content of 5 ppm/10-15 ppm A mixture of monopropylene glycol and potassium hydroxide is admixed with about 2.5 mole equivalents of propylene oxide and the resulting mixture is stirred for five hours at 130-140° C. After cooling-down of the mixture, phosphoric acid is added until a pH of 7 is reached. The resulting precipitate is filtered off. Depending on the quality of the precipitation and the filtration, residual potassium ion contents of 5/of 10-15 wppm in the polyether alcohol are determined in different batches.

The invention claimed is:

1. A process for producing a polyetheramine by reacting a polyether alcohol, previously synthesized in the presence of a basic potassium compound as catalyst, with ammonia in the presence of hydrogen and a catalyst in one reactor or a plurality of reactors, wherein the employed polyether alcohol has a content of potassium ions from 1 to 18 wppm.

2. The process according to claim 1, wherein the employed polyether alcohol has a content of potassium ions of 1 to less than 10 wppm.

3. The process according to claim 1, wherein the reaction of the polyether alcohol to afford the polyetheramine is carried out in the liquid phase at an absolute pressure in the range of from 50 to 220 bar.

4. The process according to claim 1, wherein the reaction of the polyether alcohol to afford the polyetheramine is carried out at a temperature in the range of from 150° C. to 240° C.

5. The process according to claim 1, wherein the reaction of the polyether alcohol to afford the polyetheramine is carried out using ammonia in a molar ratio per mole of alcoholic hydroxyl group in the polyether alcohol in the range of from 1.5 to 500.

6. The process according to claim 1, wherein in the reaction of the polyether alcohol to afford the polyetheramine the catalyst is arranged in the reactor/in the reactors as a fixed bed.

7. The process according to claim 1, which is carried out continuously.

8. The process according to claim 1, wherein the reaction of the polyether alcohol to afford the polyetheramine is carried out in one or more tubular reactor(s) or tube bundle reactor(s).

9. The process according to claim 1, wherein the reaction is carried out in a fresh gas mode or a cycle gas mode.

10. The process according to claim 9, wherein the reaction is carried out with a cycle gas flow rate in the range of from 50 to 1000 normal cubic meters of cycle gas/($m^3_{cat.}$·h) or a fresh gas flow rate in the range of from 1 to 200 normal cubic meters of fresh gas/($m^3_{cat.}$·h).

11. The process according to claim 1, wherein the reaction of the polyether alcohol to afford the polyetheramine is carried out at a catalyst space velocity in the range of from 0.01 to 10 kg of polyether alcohol/($l_{cat.}$·h).

12. The process according to claim 1, wherein the basic potassium compound is potassium hydroxide.

13. The process according to claim 1, wherein the polyether alcohol to be reacted is a secondary alcohol and the polyetheramine produced is a primary amine.

14. The process according to claim 1, for producing polyetheramine of the following formula by reaction of polyether alcohol of formula IIa with ammonia:

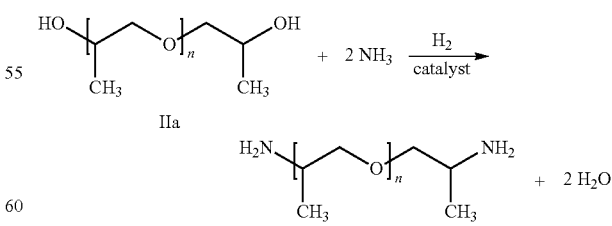

wherein the polyether alcohol and the polyetheramine are each in the form of a mixture of molecules where n is on average in the range of from 2.3 to 3.0 and the molar mass of the polyetheramine is on average in the range of from 210 to 250 g/mol.

15. The process according to claim 1 for producing polyetheramine of the following formula by reaction of polyether alcohol of formula IIb with ammonia:

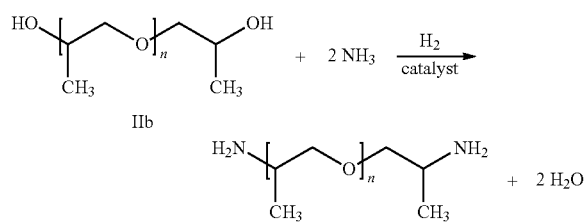

wherein the polyether alcohol and the polyetheramine are each in the form of a mixture of molecules where n is on average in the range of from 31.5 to 35.0 and the molar mass of the polyetheramine is on average in the range of from 1900 to 2100 g/mol.

16. The process according to claim 1, wherein the catalyst for the reaction of the polyether alcohol to afford the polyetheramine comprises copper and/or cobalt and/or nickel.

17. The process according to claim 1, wherein prior to its reduction with hydrogen, for the reaction of the polyether alcohol to afford the polyetheramine, the catalytically active mass of the catalyst comprises oxygen-containing compounds of aluminum and/or zirconium and/or chromium and oxygen-containing compounds of copper.

18. The process according to claim 1, wherein prior to its reduction with hydrogen, for the reaction of the polyether alcohol to afford the polyetheramine, the catalytically active mass of the catalyst comprises oxygen-containing compounds of aluminum and/or zirconium and/or chromium and oxygen-containing compounds of copper and nickel.

19. The process according to claim 1, wherein prior to its reduction with hydrogen, for the reaction of the polyether alcohol to afford the polyetheramine, the catalytically active mass of the catalyst comprises oxygen-containing compounds of aluminum and/or zirconium and oxygen-containing compounds of copper and cobalt and nickel.

20. The process according to claim 1, wherein prior to its reduction with hydrogen, for the reaction of the polyether alcohol to afford the polyetheramine, the catalytically active mass of the catalyst comprises oxygen-containing compounds of aluminum, copper, nickel and cobalt and in the range of from 0.2 to 5.0 wt % of oxygen-containing compounds of tin calculated as SnO.

21. The process according to claim 1, wherein prior to its reduction with hydrogen, for the reaction of the polyether alcohol to afford the polyetheramine, the catalytically active mass of the catalyst comprises in the range of from
    15 to 80 wt % of oxygen-containing compounds of aluminum, calculated as $Al_2O_3$,
    from 1 to 20 wt % of oxygen-containing compounds of copper, calculated as CuO,
    from 5 to 35 wt % of oxygen-containing compounds of nickel, calculated as NiO,
    from 5 to 35 wt % of oxygen-containing compounds of cobalt, calculated as CoO and
    from 0.2 to 5.0 wt % of oxygen-containing compounds of tin, calculated as SnO.

22. The process according to claim 1, wherein prior to its reduction with hydrogen, for the reaction of the polyether alcohol to afford the polyetheramine, the catalytically active mass of the catalyst comprises in the range of from
    20 to 85 wt % of oxygen-containing compounds of zirconium, calculated as $ZrO_2$,
    from 1 to 30 wt % of oxygen-containing compounds of copper, calculated as CuO,
    from 14 to 70 wt % of oxygen-containing compounds of nickel, calculated as NiO, and
    from 0 to 5 wt % of oxygen-containing compounds of molybdenum, calculated as $MoO_3$.

23. The process according to claim 1, wherein for the reaction of the polyether alcohol to afford the polyetheramine the catalyst is a cobalt-containing catalyst comprising manganese and phosphorus.

24. The process according to claim 1, wherein for the reaction of the polyether alcohol to afford the polyetheramine the catalyst is a cobalt sponge catalyst or a nickel sponge catalyst.

25. The process according to claim 1, wherein from the reaction product of the reaction, by distillation,
    (1) initially any unconverted ammonia is removed overhead,
    (ii) water is removed overhead,
    (iii) any by-products present and having a lower boiling point than the process product are removed overhead together with any remaining water,
    (iv) the process product polyetheramine is removed as bottom product.

26. The process according to claim 1, wherein the employed polyether alcohol has a content of potassium ions from 1 to 15 wppm.

* * * * *